United States Patent [19]

Grayzel

[11] Patent Number: 4,809,713
[45] Date of Patent: Mar. 7, 1989

[54] CATHETER WITH MAGNETIC FIXATION

[76] Inventor: Joseph Grayzel, 262 Fountain Rd., Englewood, N.J. 07631

[21] Appl. No.: 114,225

[22] Filed: Oct. 28, 1987

[51] Int. Cl.$^4$ .............................................. A61N 1/02
[52] U.S. Cl. ..................................... 128/785; 128/786
[58] Field of Search ................... 604/93, 64; 128/1.3, 128/1.4, 768, 784–786, 419 P

[56] References Cited

U.S. PATENT DOCUMENTS

| | | |
|---|---|---|
| 1,089,805 | 3/1914 | Wolf . |
| 1,596,754 | 8/1926 | Maschelle . |
| 1,696,018 | 12/1928 | Schellberg . |
| 2,863,458 | 12/1958 | Modny et al. . |
| 3,043,309 | 7/1962 | McCarthy .................. 128/1.4 X |
| 3,433,215 | 3/1969 | Silverman . |
| 3,490,457 | 1/1980 | Peterson . |
| 3,568,679 | 3/1971 | Reif . |
| 3,605,749 | 9/1971 | Heimlich . |
| 3,640,281 | 2/1972 | Robertson . |
| 3,656,486 | 4/1972 | Robertson . |
| 3,674,014 | 7/1972 | Tillander .................. 128/1.3 X |
| 3,703,174 | 11/1972 | Smith . |
| 3,794,041 | 2/1974 | Frei et al. . |
| 3,961,032 | 6/1976 | Moossun .................. 128/1.3 X |
| 4,026,302 | 5/1977 | Grayzel . |
| 4,154,227 | 5/1979 | Krause et al. . |
| 4,292,974 | 10/1981 | Fogarty et al. . |
| 4,702,146 | 2/1978 | Howes . |

FOREIGN PATENT DOCUMENTS 1261276 2/1968 Fed. Rep. of Germany .

OTHER PUBLICATIONS

The Pod and its Applications by E. H. Frei et al., 1966, pp. 11–18.

*Primary Examiner*—Stephen C. Pellegrino
*Attorney, Agent, or Firm*—Weingram & Zall

[57] ABSTRACT

The present invention involves catheters used for electrical pacing or excitation of the heart where critical placement and firm contact within the inner wall of the heart is required. The invention meets the requirement in the case of pacing catheters in the electrode at the catheter tip which maintains a firm, constant contact pressure against the inner surface of the heart's muscular wall despite the beating and movement of the heart. The invention provides a mechanism whereby the electrode tip actually presses against the heart with constant pressure resulting in a much more effective and desirable operation. A first magnet is positioned at or near the electrode tip of the pacing catheter and a second passive or holding magnet is fixed to the chest of the use to provide a magnetic force to position the tip of the pacing catheter.

The invention also sets forth a method for positioning the passive or holding magnet to optimize the magnetic effect that will hold the electrode tip of the pacing catheter in position.

14 Claims, 2 Drawing Sheets

CATHETER WITH MAGNETIC FIXATION

BACKGROUND OF THE INVENTION

1. Field of the Invention

This invention relates to catheters and specifically to those catheters utilized in electrical pacing or excitation of the heart which require critical placement and firm contact with the inner wall of the heart.

1. Description of the Prior Art

A catheter is a tubular device that is placed within channels, hollow spaces or chambers of the human body. Catheters are generally flexible, hence, maintaining the position of the catheter tip at the desired location for long periods of time is not assured. Various means have been incorporated in the distal tip of catheters to perform fixation. These means include inflatable balloons, suture devices, screw-in connectors and the like. In addition to such mechanical means of fixation, attempts have also been made to employ magnetic means to either directly locate or secure the catheter with respect to the desired location in the body.

Problems concerning such catheters are especially severe for those catheters used in heart pacing and excitation. Failure to maintain critical placement and firm contact of the catheter tip with the inner wall of the heart can result in loss of capture and therefore serious consequences to the operation of the heart of the patient.

Peterson U.S. Pat. No. 3,490,457 is exemplary of a mechanical arrangement for securing a catheter in the bladder or other body cavity. The securing system employs a flexible sleeve which is expandable and retractable. When expanded, the catheter is retained in position and, when retracted, the catheter can be inserted or removed.

Reif, U.S. Pat. No. 3,568,679 mechanically secures a catheter in place by the use of a thin disc of silicon rubber adhesively secured to an external surface of the body. The disc has a locking device which secures the catheter in place externally after it is inserted and reaches the desired position in the body.

Tillander, U.S. Pat. No. 3,674,014 describes a flexible tip catheter which is guided by a magnetic field. A plurality of permanent magnet tubular sections with ball-shaped ends are arranged end to end on the tip of the catheter. This provides the necessary magnetic bendable, flexible tip required to position the catheter.

German Pat. No. 1,261,276 shows use of an external magnet to attract the internal magnet on the distal end of a catheter to a desired point in colonoscopy.

U.S. Pat. No. 2,863,458 to Modny et al. utilizes a magnetic plumb at the end of a nylon line. An external magnet attracts the magnetic plumb, drawing it along the length of a vein, thereby positioning a vein stripper through the vein.

U.S. Pat. No. 3,043,309 to McCarthy discloses an apparatus for performing intestinal intubation and is useful in the procedure called "decompression". A magnet is secured to the tip of an elongated x-ray opaque flexible tube. The tip and tube are then passed through the oesophagus to the stomach of the patient. The stomach is then observed fluoroscopically. A maneuverable magnetic field is then applied to the magnetic material to direct the tip to the pyloric valve in the stomach.

Magnetic fixation of catheters is shown in Moossun's U.S. Pat. No. 3,961,632. There, a trans-abdominal stomach catheter placement system involves a novel magnetic intubation device to distend or advance the forward portion of the stomach wall into relatively close proximity to the exterior abdominal wall.

An article, THE POD AND ITS APPLICATIONS by Frei et al., 1966 *Medical Research Engineering* pages 11-18, discusses the use of externally driven magnets which are used to control the passage of catheters to a desired location via what the article terms "a pod magnet in a catheter".

The prior art using magnets shown in some of the above patents and the article all involve the use of an external positioning magnet to propel and/or position, or both, the catheter within the body. The application of magnetic means to locating and securing the stimulating electrode of a pacemaker catheter has not been taught or suggested in the prior art.

SUMMARY AND OBJECTS OF THE INVENTION

The present invention involves catheters used for electrical pacing or excitation of the heart where critical placement and firm contact within the inner wall of the heart is required. The invention meets the requirement in the case of pacing catheters with the electrode at the catheter tip which maintains a firm, constant contact pressure against the inner surface of the heart's muscular wall despite the beating and movement of the heart. The invention provides a mechanism to magnetically position and secure the electrode tip so that the electrode tip actually presses against the heart with constant force resulting in a much more effective and desirable operation. A first magnet is positioned at or near the electrode tip of the pacing catheter and a second passive or holding magnet is fixed to the chest of the user to provide a magnetic force to position the tip of the pacing catheter.

The invention also sets forth a method for positioning the passive or holding magnet to optimize the magnetic effect that will hold the electrode tip of the pacing catheter in position.

A principal object of the present invention is the provision of the desired fixation of the catheter tip, particularly the electrode at the tip of a pacing catheter, without employing mechanical means, thereby avoiding trauma to the local tissues.

It is a further object of the present invention to provide a fixation means at the tip of the catheter capable of adjusting the contact pressure between the catheter tip and the adjacent tissue.

Another object of the present invention is to provide a mechanism for providing fixation of a catheter tip which does not involve the use of any external electromagnetic fields or generation equipment.

A further object of the present invention is the provision of a fixation system where the electrode tip of the catheter utilized on the human heart will not be subject to disruption of contact by the beating of the heart or other movement thereof.

Another object of the invention is the provision of a device for detecting the position of the magnetic tip of the catheter and hence enabling accurate positioning of the fixed or holding magnet.

A further object of the invention is the development of a method and apparatus for positioning the passive or holding magnet at the desired location.

These as well as other objects and advantages of the present invention will become apparent to those skilled

DETAILED DESCRIPTION OF THE INVENTION

In brief, the system employs two magnets: a first magnet, also denoted as the active magnet, oriented within or at the catheter tip; and a second magnet, also denoted as the passive or holding magnet, placed on the skin or implanted beneath the skin in the area just overlying and adjacent to the first magnet within the body.

Figure 1:
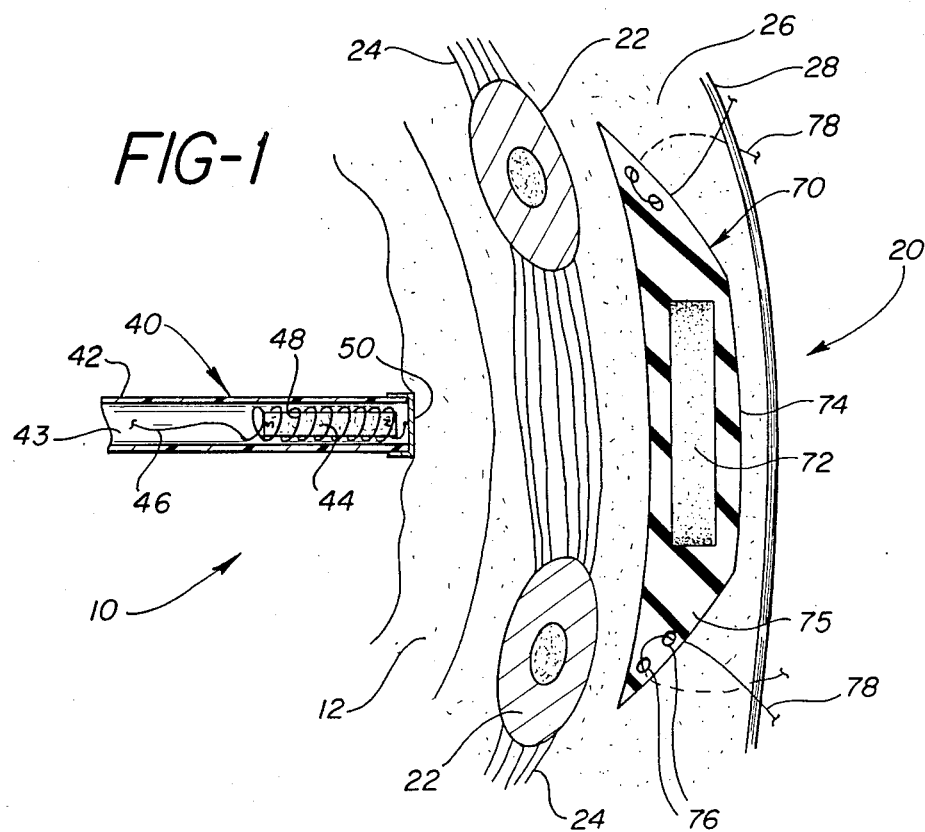
FIG. 1 is a diagrammatic view of the catheter magnetic tip mounted within the human heart and the cooperating magnet mounted subcutaneously within the chest wall external to the rib cage.

As shown in FIG. 1, a catheter generally indicated at 40 is positioned within the heart generally indicated 10 and in contact with the heart wall 12. The heart is adjacent the chest wall generally indicated at 20 having ribs 22 and intercostal muscle 24. Subcutaneous tissue 26 is covered by external skin 28. The catheter 40 has cylindrical walls 42 and may have a lumen 43. A magnet 44 of cylindrical shape is disposed near the end of the catheter. Conductive insulated wire 46 wraps around the magnet 44 to form a coil 48 and the end of the wire contacts the conductive tip or electrode 50 of the catheter to contact the heart. Positioned within the chest wall is a larger passive or immobile or holding magnet assembly, generally indicated at 70, having a magnetic disk 72 mounted within a housing 74 to protect the magnet from contact with the subcutaneous tissue 26 and body fluids and to allow for fastening or the magnet beneath the skin by means of suture holes 76 disposed on the periphery of the housing 74 with sutures 78 that fasten the housing to the skin or the subcutaneous tissue.

In the preferred embodiment shown in FIG. 1, the first or active magnet 44 is a cylinder with an axial dimension which is relatively long compared to its diameter. The longitudinal axis of magnet 44 is coincident with or parallel to the axis of the tubular catheter 40. The diameter of the second, passive or holding magnet, the disk magnet 72, is very much greater than the axial dimension or thickness thereof. The disk magnet 72 has been found to be a stable shape for the attachment on or implantation beneath the skin. Since the diameter of the passive magnet 72 is large with respect to the diameter of the cylindrical or active magnet 44, assurance is obtained that different locations of the magnet 44 will be within the magnetic field of the second magnet 72 so that precise positioning of the magnet 44 is not required and is nor critical for the holding force which is to be exerted.

In addition, housing 74 of the passive magnet should be visibly marked with respect to polarity so that it can be placed and located by the surgeon to generate an attractive force relative to the magnet 44.

If the catheter must employ a lumen or channel within its tubular shape, the lumen may exit behind the magnet via one or more side holes 52 in the catheter wall. Alternatively, if the lumen must travel straight through the catheter tip, the embodiment of FIG. 3 may be employed.

Figure 3:
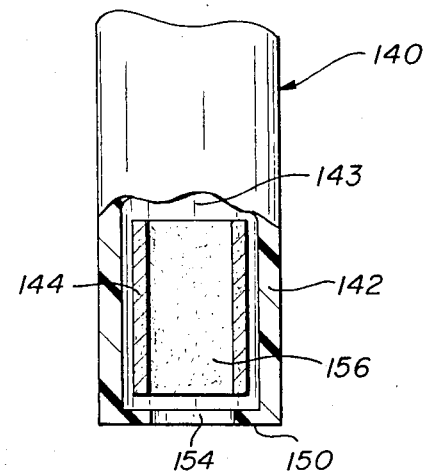
FIG. 3 is an alternate embodiment of a catheter tip for use in the present invention.

As shown in FIG. 3, a catheter, generally indicated at 140, has walls 142 surrounding a lumen 143 with a magnet 144 positioned at the tip of the catheter. The magnet 144 is a cylindrical shell magnet located near the tip of the catheter and is held in by the tip 150 of the catheter through which an aperture 154 is formed. The aperture 154 at the tip of the catheter 150 aligns with the aperture 156 in the tubular magnet 144 to connect with the lumen of the catheter 143.

When used with pacing catheters, the helical conductive coil 48 formed from wire 46 which conveys the electrical signal to the electrode or tip 50 of the catheter, has a preferential direction of rotational pitch which produces the same polarity as the magnet 44 so as to increase the field strength of the magnet. As the conductive wire forms a spiral coil 48 around the magnet 44, the field generated in the coil thus created must be additive to the field of the magnet during the brief time when the stimulating electrical current flows to the tip electrode. Thus, the magnetic field and the force tending to seat the catheter tip is augmented.

As shown in FIG. 1, the passive magnet assembly 70 is surgically implanted within the skin 20. Passive magnet 72 is disposed in housing 74 which has suture holes 76 circumferentially disposed on the housing. After the magnet 72 is implanted, magnet 44 presses against the heart wall 12 with a force dependent on the strength of both magnets 44 and 72 and the distance between magnets 4 and 72. Generally, the use of x-ray permits a determination of the distance between respective sites so that selection of passive magnet 72 of appropriate strength provides the desired contact force between the tip 50 of catheter 40 and the heart wall 12.

For greater conformability to body contours, passive magnet 72, and/or its housing 74, may possess some curvature rather than being planar. The corners of magnet 72 and/or its housing 74 may similarly be rounded. The housing 74 may be formed of a nonreactive material, such as medical grade silicon rubber. As shown in FIG. 1, housing 74 has a skirt section 75 to provide suture holes 76 to permit securing of the second magnet 72 in place. The skirt is tapered to avoid any corners or prominences facing the skin which might contribute to pressure erosion of the skin. In the preferred embodiment, the housing 74 and skirt section 75 are curved to conform to body contours. This curvature acts as an indicia to position the housing to produce proper polarity of the magnetic field of the magnet in the housing with respect to the magnet in the tip of the catheter. In addition, the broader surfaces on opposite sides of the passive magnet may have visual indicia thereon to indicate which surface should be mounted inward towards the heart and which surface should face outward towards the skin.

Figure 2:
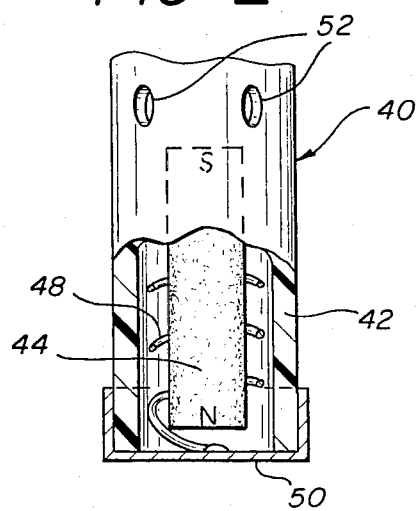
FIG. 2 is a sectional view of the catheter tip employed in the embodiment of FIG. 1.

In the use of the device of FIGS. 1-3, it is important that passive magnet 72 implanted subcutaneously be positioned over active magnet 44 which resides within the tip of catheter 40. Furthermore, it is optimum that the second magnet 72 is precisely centered over active magnet 44, i.e coaxial with magnet 44. A method and apparatus is provided which enables the surgeon to accomplish this location even in the absence of x-ray or other means of direct visualization. Even where direct visualization is available, the method and apparatus described herein permits positioning of the passive magnet with great precision, speed and facility.

For the purpose of describing the method herein, the opposite poles of a cylindrical magnet are denoted N and S respectively. Like poles repel and opposite poles attract one another.

Figure 5:
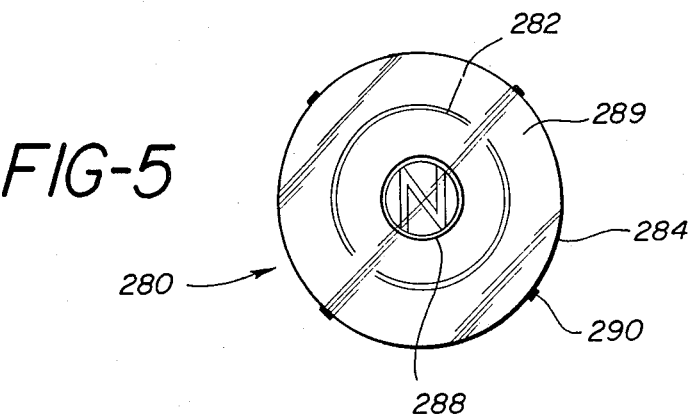
FIG. 5 is a top view of the positioning device shown in FIG. 4.
Figure 4:
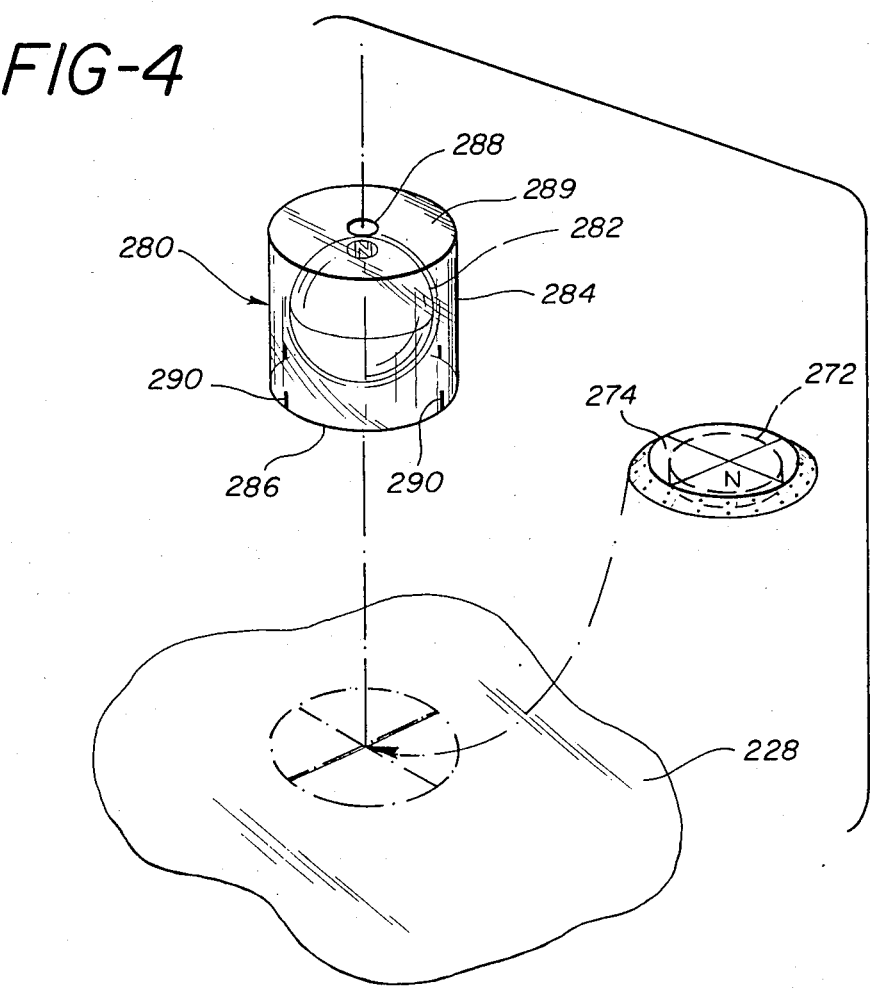
FIG. 4 is a perspective view of the positioning device employed to locate the catheter tip in the heart and position the holding magnet.

The method and apparatus for positioning the passive magnet are shown in FIGS. 4 and 5. A transvenous catheter with a magnet at its tip is positioned at the apex of the right ventricle in the usual manner for cardiac pacing. The catheter is fabricated with the N pole of the magnet facing towards the catheter tip. Precise positioning of the passive or second magnet 272 relative to the external surface of the skin 228 is determined with the use of a magnetic finder generally indicated at 280 compass-like device of spherical form capable of rotation in all three geometric planes, possessing a clearly visible mark at its N pole.

The spherical rotatable compass 282 is supported by a housing 284 with a circular base of diameter equal to that of the magnet housing 274 of passive magnet 272. Above the spherical compass, the housing possesses an uppermost planar surface 288 of transparent material (i.e. plastic or glass), oriented in a plane parallel to the plane of the circular base 286. Inscribed at the center of this uppermost transparent surface is a circle identical in size to the aforesaid mark on the N pole of the spherical compass. The relationship between the uppermost transparent surface with inscribed circle, spherical compass, and circular base is such that if from the center of said circle on the uppermost surface, a line is constructed perpendicular to the circular base, such line passes through the center of the spherical compass and meets the circular base in the center of the circle formed by its perimeter.

To determine the optimum location for implantation of the second magnet 272, the housing 284 of the compass is moved over the skin surface 228, its base resting on the skin, and the N pole mark observed through the transparent surface relative to the circle inscribed thereon. When the N pole mark lies precisely within the projection of said circle, the S pole of the compass is directly over the N pole of the magnet within the tip of catheter. Then a pen, suitable for marking the skin, inscribes a circle around the base of said compass device 290 or by marks on the skin at the location of the four indicia grooves 290 of the housing 284 thereby identifying the optimum position for implantation of the encapsulated magnet 272. An incision is made in the skin across a true diameter within the circular skin marking. A subcutaneous space or pouch is dissected corresponding to the circular skin marking. The encapsulated second of passive magnet is implanted therein, oriented according to the visual means indicating which surface must face the heart and which surface must face outward toward the skin. This indication means is so disposed to direct the S pole of magnet 272 towards the heart hence towards the N pole of the active magnet within the heart. Then, magnet 272 via its encapsulation or housing 274 is secured in place by suture means passing through suture holes 276 around the periphery of the encapsulation or housing 274 and into the subcutaneous tissue. Lastly, the skin is suture closed over the magnet housing 274 utilizing conventional suturing means and techniques.

As shown in FIG. 5, the indicia for the spherical compass and the indicia 288 on the top surface 289 of housing 284 line up to form concentric circles to that any variation from the vertical of the N pole can easily be sensed by the difference in the position of the concentric circles about the N of the compass and the circle at the top of the housing.

While several embodiments of the invention have been illustrated and described, it is apparent that many other variations may be made in the particular design and configurations shown herein without departing from the scope of the invention set forth in the appended claims.

I claim:

1. Apparatus for maintaining a pacing catheter adjacent the interior wall of the heart, said apparatus comprising:
   a "pacing" catheter having a distal end;
   a first magnet mounted in the distal end of said "pacing" catheter in proximity to the heart;
   a second magnet disposed outside the chamber of the heart;
   means to fix the position of said second magnet to the body; and
   said first and second magnets exerting a force for maintaining the position of the tip of said catheter against the wall of the heart.

2. The apparatus according to claim 1 wherein said first magnet has a configuration having relatively long longitudinal axis and a relatively small diameter.

3. The apparatus according to claim 1 wherein said second magnet has a relatively large diameter and relatively small thickness.

4. The apparatus according to claim 1 wherein said first magnet has a configuration having relatively long longitudinal axis and a relatively small diameter and said second magnet has a relatively large diameter and relatively small thickness.

5. The apparatus according to claim 1 wherein said catheter includes a lumen centrally located along the length of said catheter.

6. The apparatus according to claim 5 wherein said magnet mounted in the distal end of said catheter is in the form of a hollow cylinder surrounding said lumen.

7. The apparatus of claim 1 wherein said catheter further includes conductive wiring forming a coil around the magnet mounted at the distal end of said catheter in proximity to the heart so that electricity going to the distal end of the catheter will form a magnetic field that reinforces the magnetic field of the magnet mounted at the distal end of said catheter.

8. The apparatus according to claim 1 wherein said second magnet is disposed outside the ribs of the chest wall.

9. The apparatus of claim 1 wherein said second magnet is encapsulated in a medical grade encapsulation material, said capsule having ends thereon with suture holes formed therein for adhering said encapsulated second magnet to the tissue.

10. The apparatus according to claim 8 wherein said second magnet is disposed within a housing and said housing is shaped to conform with the curvature of the chest wall.

11. The apparatus according to claim 10 wherein the curvature of the housing is coordinated with the polarity of the holding magnet enclosed therein to ensure that the holding magnet will be installed to attract the first magnet in the distal end of the catheter.

12. The apparatus according to claim 10 wherein the housing includes a skirt section which is tapered to minimize pressure erosion of the tissue adjacent said housing.

13. A method for positioning and maintaining a catheter in the heart comprising the steps of:
   positioning a catheter in the heart with a distal end touching the appropriate portion of the heart wall;
   said distal end of said catheter including a permanent magnet to form a magnetic field about said distal end of said catheter;
   locating the position of said magnet in said distal end of said catheter by moving a magnetic finder device over the surface of the skin adjacent to the magnet positioned in the distal end of the catheter within the heart; and
   fixing a holding magnet on the body outside the heart in place.

14. The method for positioning and maintaining a catheter in the heart according to claim 13 wherein the step of fixing a holding magnet on the body outside of the heart includes the steps of:
   incising the skin to make a pouch for insertion of a holding magnet at the location determined to be adjacent to the distal end of the catheter;
   inserting the holding magnet in said pouch;
   fixing the holding magnet in place in relation to the surrounding tissue; and
   closing the incision.

* * * * *